United States Patent [19]

Shelton et al.

[11] Patent Number: 5,527,347

[45] Date of Patent: Jun. 18, 1996

[54] DUAL CHAMBER PACING SYSTEM AND METHOD WITH AUTOMATIC ADJUSTMENT OF THE AV ESCAPE INTERVAL FOR TREATING CARDIOMYOPATHY

[75] Inventors: Michael B. Shelton, Minneapolis; Dwight H. Warkentin, St. Paul, both of Minn.

[73] Assignee: MedTronic, Inc., Minneapolis, Minn.

[21] Appl. No.: 391,884

[22] Filed: Feb. 21, 1995

[51] Int. Cl.⁶ ............................................. A61N 1/362
[52] U.S. Cl. ................................................... 607/9
[58] Field of Search .................................. 607/9, 28, 17, 607/25

[56] References Cited

U.S. PATENT DOCUMENTS

| | | |
|---|---|---|
| 4,428,378 | 1/1984 | Anderson . |
| 5,052,388 | 10/1991 | Sivula et al. . |
| 5,086,774 | 2/1992 | Duncan ........................................ 607/9 |
| 5,144,950 | 9/1992 | Stoop et al. ................................. 607/9 |
| 5,334,220 | 8/1994 | Sholder . |
| 5,340,361 | 8/1994 | Sholder . |

OTHER PUBLICATIONS

McDonald, Kenneth et al., "Permanent Pacing as Treatment for Hypertrophic Cardiomyopathy", The American Journal of Cardiology, vol. 68, Jul. 1991, pp. 108–110.

Jeanrenaud, Xavier et al., "Effects of Dual–Chamber Pacing in hypertrophic Obstructive Cardiomyopathy," The Lancet, vol. 339, May 1992, pp. 1318–1323.

McAreavey, Dorothea et al., "Altered Cardiac Hemodynamic and Electrical State in Normal Sinus Rhythm After Chronic Dual–Chamber Pacing for Relief of Left Ventricular Outflow Obstruction in Hypertrophic Cardiomyopathy", American Journal of Cardiology, vol. 7, Sep. 1992, pp. 651–656.

Seidelin, P. H., "Effects of Dual–Chamber Pacing in Hypertrophic Cardiomyopathy without Obstruction", The Lancet, vol. 340, Aug., 1992, pp. 369–370.

Boute, W., et al., "Morphology of Endocardial T–Waves of Fusion Beats", PACE, vol. 11, Nov. 1988, Part II, pp. 1693–1697.

Fananapazir, et al., "Impact of Dual Chamber Permanent Pacing in Patients with Obstructive Hypertrophic Cardiomyopathy with Symptoms Refractory to Verapamil and β–Adrenergic Blocker Therapy", Circulation, vol. 8, No. 6, Jun. 1992, pp. 2149–2161.

Primary Examiner—William E. Kamm
Assistant Examiner—Kennedy J. Schaetzle
Attorney, Agent, or Firm—Michael B. Atlass; Harold R. Patton

[57] ABSTRACT

There is provided a dual chamber pacemaker system and method for ventricular pacing to provide therapy for a patient with cardiomyopathy, this system being characterized by automatically adjusting the AV escape interval so that ventricular pace pulses are delivered at an AV delay which is optimized for HOCM and/or dialated cardiomyopathy therapy. The pacemaker system continually obtains and stores representations of a QRS wave characteristic such as duration, derived either directly from the QRS signal or from an FFRS signal, and compares duration data from one or more cycles to prior stored duration data. The system then adjusts the AV interval as a function of the duration comparison, and the direction of the last adjustment of AV escape interval. By this means, the AV escape interval is maintained at or just short of the onset of fusion, thereby automatically providing for optimally lengthened AV escape intervals consistent with full capture by the delivered ventricular pace pulse.

20 Claims, 6 Drawing Sheets

DUAL CHAMBER PACING SYSTEM AND METHOD WITH AUTOMATIC ADJUSTMENT OF THE AV ESCAPE INTERVAL FOR TREATING CARDIOMYOPATHY

BACKGROUND OF THE INVENTION

This invention Relates to cardiac pacing systems and methods generally and, in particular, to dual chamber cardiac pacing systems and methods for delivering ventricular pacing pulses synchronized to atrial signals so as to benefit patients with various forms of congestive heart failure (CHF) and in particular patients with Hypertrophic Obstructive Cardiomyopathy.

Hypertrophic Obstructive Cardiomyopathy (HOCM) is characterized by a narrowed left ventricular outflow tract (LVOT), which causes a significant increase the subaortic pressure gradient. The narrowed LVOT is caused by an increased thickess of the interventricular septum which obstructs blood flow during systole, or at the time of cardiac output.

Symptomatic improvement of patients with HOCM can be obtained in some cases with the use of standard pharacotherapy. However, drugs in use for this therapy have disadvantages which have been cited in the literature. Likewise, surgical intervention, e.g., septal myectomy of initial valve replacement, is another optional treatment. However, such surgical treatments carry a significant operative mortality and have not been shown to alter the natural history of the disease. See, "Permanent Pacing As Treatment For Hypertrophic Cardiomyopathy," by Kenneth M. McDonald et. al., *American Journal of Cardiology*, Vol. 68, pp. 108–110, July 1991.

The value of dual chamber cardiac pacing and treatment of patients suffering from HOCM has been recognized in the literature. Modern multiple-mode, dual-chamber cardiac pacemakers are designed to maintain AV syncrony for damaged or diseased hearts that are unable to do so on their own. For example, a DDD pacemaker has electrical connections to both the atrium and the ventricle, senses electrical signals in both chambers of the patient's heart, and delivers atrial pacing stimuli in the absence of signals indicative of natural atrial contractions, and ventricular pacing stimuli in the absence of signals indicative of natural ventricular contractions. Such a dual chamber pacemaker maintains the AV synchrony of the heart by delivering ventricular pace pulses at a controlled AV interval following each atrial event.

Studies have indicated that patients suffering from HOCM may benefit from a specific mode of dual chamber pacing wherein a ventricular pace pulse is delivered in timed synchrony with the sensed or paced atrial depolarization. Pacing the right ventricular apex before spontaneous atrioventricular conduction activates the left ventricle is understood to alter the ventricular septal activation pattern. Since the right ventricle is caused to contract first, it is believed that it pulls the septum toward the right ventricle, thereby reducing the LVOT obstruction and subaortic pressure gradient. Other mechanisms have been hypothesized but in any event timed synchrony produces a benefit.

The literature uniformly acknowledges the potential advantages of synchronized A-V pacing for HOCM patients, stressing the importance of achieving ventricular capture. Causing "complete ventricular capture" is important to obtain the above-described septal movement, while selecting the longest AV delay that results in complete ventricular capture is important in order to maximize the atrial contribution to ventricular filling. See U.S. application Ser. No. 08/214,933, filed Mar. 17, 1994, Method and Apparatus For Dual Chamber Cardiac Pacing, assigned to Medtronic, Inc. now U.S. Pat. No. 5,507,792, and the literature articles referenced therein. The delivered pace pulse should provide "pre-excitation," i.e., depolarization of the ventricular apex before the septum. This altered pattern of septal contraction, as well as optimal left ventricular filling, is generally recognized as being important to this mode of pacemaker treatment. Further, it appears to be established that such synchronized AV pacing provides HOCM patients a long term benefit, i.e., the benefit remains even after cessation of pacing, since such AV pacing causes a reduction in the obstruction of the LVOT which persists in sinus rhythm after cessation of pacing.

The literature suggests that the AV escape interval should be set at the longest duration that maintains ventricular capture at different exercise levels. See the above-cited McDonald article. It has been suggested that the AV escape interval which allows for maximal pre-excitation of the ventricle by the pacing pulse can be selected by determining the AV escape interval that produces the widest paced QRS complex duration. See "Impact of Dual Chamber Permanent Pacing in Patients With Obstructive Hypertrophic Cardiomyopathy With Symptoms Refractory to Verapamil and β Adrenergic Blocker Therapy," by Fananapazir et al., *Circulation*, Vol. 8, No. 6, June 1992, pp. 2149–2161.

In the referenced U.S. application assigned to Medtronic, Inc., the pacemaker periodically checks to determine a value of intrinsic AV conduction time (AVC) and subtracts therefrom a ventricular sense offset interval (VSO) to get the AV escape interval. After a waveform of the ventricular alepolarization resulting from complete capture is noted and recorded for comparison, the AV escape interval is set to a lengthened value, resulting in one or more ventricular sense events. The value of AVC is determined as the time difference between the atrial event and the sensed R-wave. Following this, the pacemaker AV escape interval is reduced further until the pacemaker finds an R wave with a waveform that indicates good capture. The difference between AVC and the capture value of A-V is VSO; and the pacemaker thereafter sets AV=AVC–VSO.

The prior art techniques for synchronous pacing of HOCM patients recognize the necessity to periodically evaluate the AV delay, or AV escape interval. The patient's spontaneous atrio-ventricular conduction time generally will change with heart rate, i.e., from rest to exercise. Moreover, simultaneous drug treatment such as beta blockers may also modify AV conduction time and require renewed evaluation of the AV delay. The importance of periodically making an accurate determination of the optimized AV interval thus takes on significance. If the AV delay is adjusted to a value which is too short, in order to ensure complete ventricular capture, the atrial contribution to ventricular filling is compromised. However, if the AV escape interval is adjusted to too great a value, ventricular capture is compromised, and there may be episodes of no ventricular pacing or the ventricular pace may not contribute the best possible reduction of the LVOT obstruction. Accordingly, it is important in this therapy to be able to continuously or periodically adjust the AV escape interval to optimize it for HOCM and related or similar congestive heart failure therapies.

SUMMARY OF THE INVENTION

The pacemaker system and method of this invention provide closed loop automatic adjustment of the AV escape interval so as to maintain it in a narrow range corresponding to optimal pre-excitation. The invention utilizes either the QRS signal detected on the V-sense channel (including either intrinsic or paced QRS), or the far field R-wave signal (FFRS) detected on the A-sense channel, and continually and automatically adjusts the AV escape interval on the basis of the detected signals so as to optimize the timing of the ventricular pace pulse for pre-excitation.

More specifically, the pacemaker system and method of this invention utilize the observation that the duration of the evoked QRS, manifested either by the sensed QRS or FFRS, has a duration which peaks corresponding to an AV delay just less than the intrinsic AR or PR value, and in about the fusion range. Specifically, the plot of QRS duration versus pacemaker AV delay reveals that at AV values well less than the patient's intrinsic conduction value, corresponding to complete capture by ventricular pace pulses, the evoked QRS duration is substantially constant. As AV escape interval ($AV_{esc}$) is increased, the QRS duration increases to a maximal point, corresponding roughly to the onset of fusion, and then decreases to a lower and constant value, corresponding to intrinsic conduction and failure to pace. This invention takes advantage of this observation by providing a closed loop control to maintain the pacemaker AV delay in the area of the maximal duration, thus keeping AV delay in a small range around or below values corresponding to fusion, thereby optimizing pre-excitation and HOCM or CHF therapy.

DETAILED DESCRIPTION OF THE PREFERRED EMBODIMENTS

Figure 1:
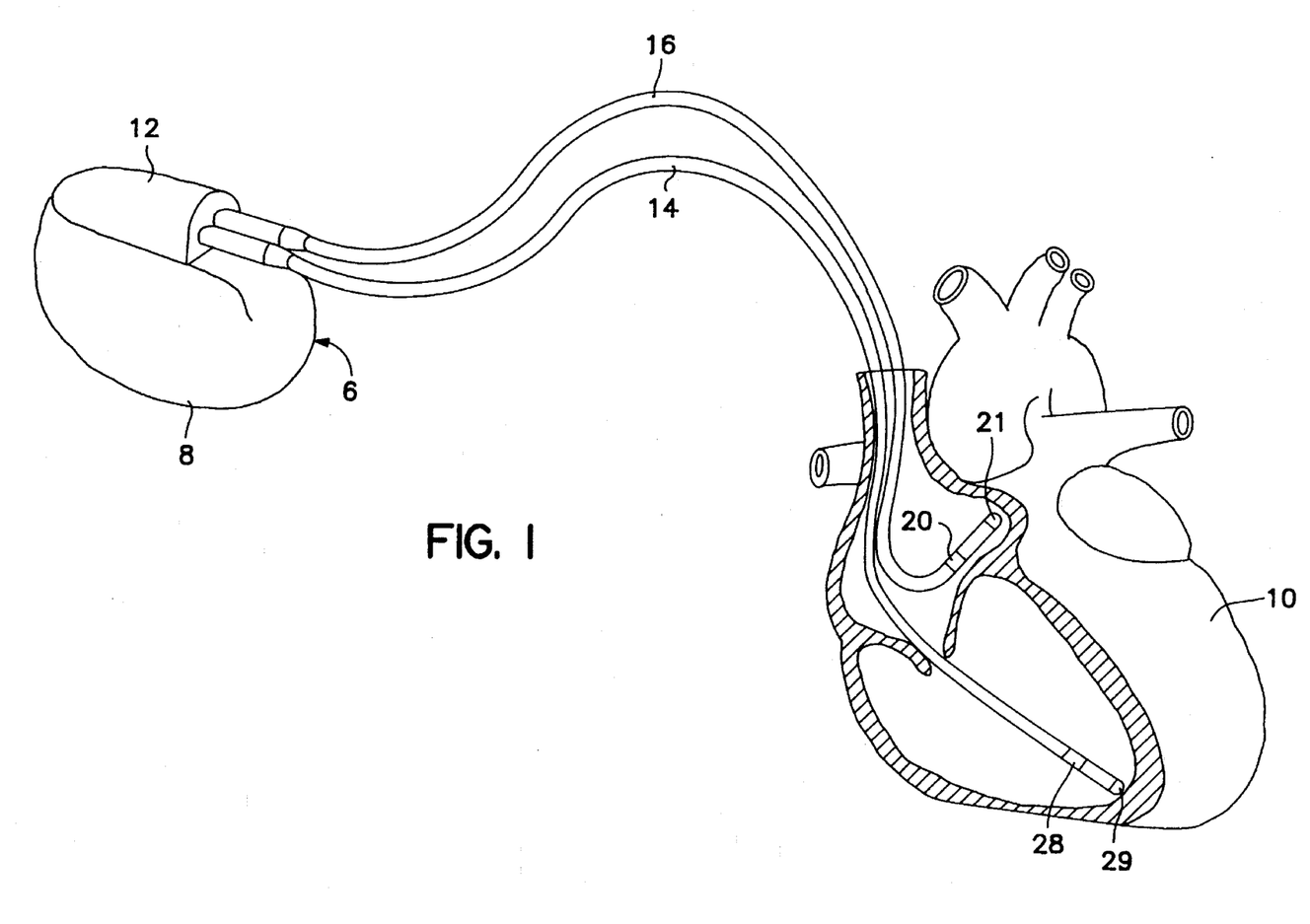
FIG. 1 is a perspective representation of the pacemaker system of this invention showing an implantable pacemaker connected to a patient's heart.

FIG. 1 illustrates the external configuration of a dual chamber pacemaker 6, which is provided with a hermetically sealed enclosure 8, typically fabricated of biocompatible metal such as titanium. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrode 20 and 21 and the housing 8 of the pacemaker 6.

Similarly, lead 14 represents a ventricular bipolar pacing lead, carrying two electrodes 28 and 29. As discussed above in conjunction with atrial lead 16, electrodes 28 and 29 are used to sense and pace the ventricle. Ventricular pacing may be accomplished between electrodes 29 and 28 or between electrode 29 and the conductive housing 8 of pacemaker 6. Sensing of ventricular signals, including depolarizations (QRS-waves) and repolarizations (T-waves) may be accomplished between electrodes 29 and 28 or between either of electrodes 29 and 28 and the housing 8 of the pacemaker 6.

As discussed in the present application, the preferred embodiments of the pacemaker 6 operate in a DDD or DDDR pacing mode, wherein pacing pulses are delivered to both atrium and ventricle and wherein atrial and ventricular depolarizations are both effective to inhibit delivery of the next scheduled pacing pulse in the chamber in which they are detected. While the present invention is believed optimally practiced in a pacemaker operating in DDD pacing mode, in some patients there may also be a benefit to operating the device in VDD or DVI mode, which provides ventricular pacing pulses synchronized only to sensed atrial depolarizations or only delivered to atrial pacing pulses, respectively, depending upon the specific underlying heart condition of the patient. However, DDD mode is expected to be the mode most widely used to practice the present invention.

Figure 2:
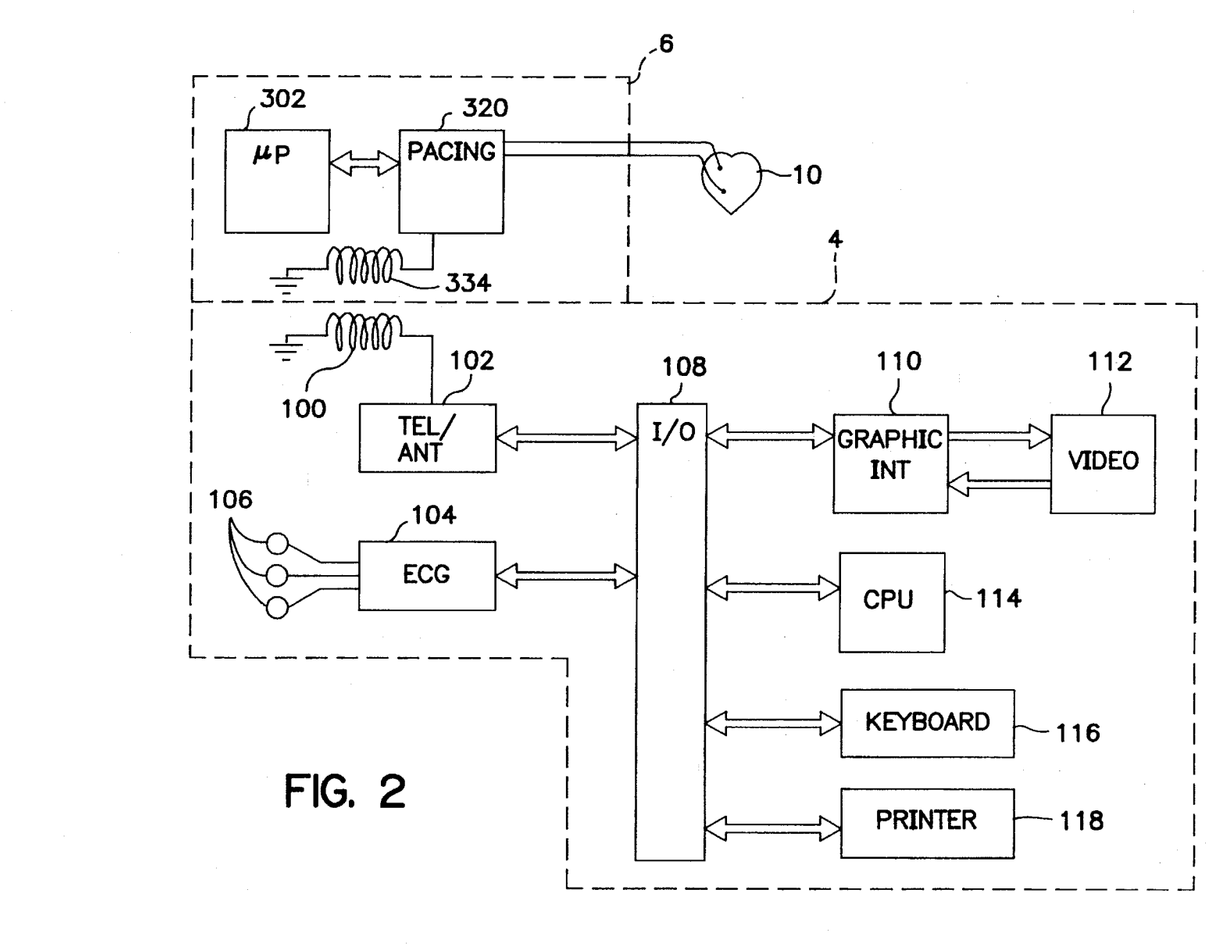
FIG. 2 is a block diagram of the pacemaker system of this invention, showing a pacemaker inter-connected with an external programmer and with ECG leads.

FIG. 2 illustrates the pacemaker 6 in block diagram form, coupled to a human heart 10, in conjunction with an external programmer/display apparatus corresponding to those typically employed to program modern, multi-programmable implantable pacemakers. Within the housing of the pacemaker are located the pacing circuitry 320, which includes circuitry performing all of the basic timing, stimulation and sensing functions of a cardiac pacemaker and a microprocessor circuit 302, which controls the timing intervals provided by the pacing circuitry 320. Pacing circuitry 320 also includes a bidirectional telemetry circuit coupled to an antenna 334, allowing transmission of information from external programmer 4 into the pacemaker 6 to modify its parameters and allowing transmission of information from the pacemaker 6 to the external programmer 4, again generally corresponding to telemetry and programming systems presently existing in commercially marketed multi-programmable in implantable pacemakers.

The programmer 4 also includes a corresponding antenna 100 coupled to a telemetry/antenna driver circuit 102 which serves to demodulate telemetry signals received from antenna 334 of the pacemaker, and to apply them in parallel or serial digital format to input output (I/O) unit 108, where they in turn may be applied to a video monitor 112 via graphic interface 110, and/or provided to central processing unit 114 and/or printer 118. Microprocessor 114 controls the operation of the programmer/display apparatus, and is responsive to physician entered commands via keyboard 116, for controlling programming signals sent to the pacemaker, as well as for controlling operation of the video display 112 and printer 118. Also illustrated is an ECG interface 104, coupled to three ECG electrodes 106 which can be placed upon the patient's body. ECG interface 104 provides sensed electrograms to input/output device 108, where they in turn may be provided to the video display 112, the central processing unit 114 or the printer 118. The ECG capability is used for treatment according to the method of this invention for a patient who is available for initial or subsequent programming.

Figure 3:
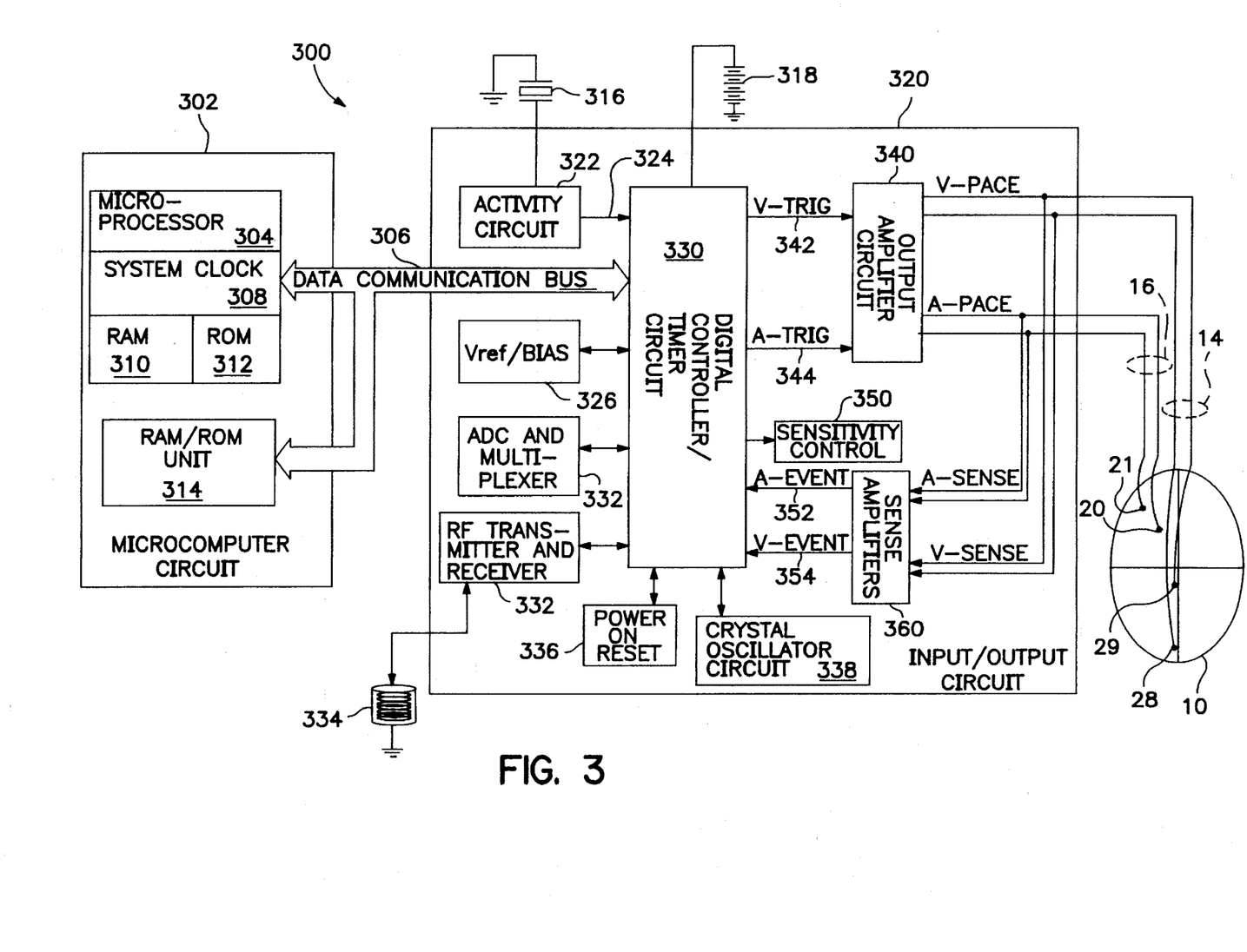
FIG. 3 is a block diagram of the primary functional components of a pacemaker used in the system and method of this invention.

FIG. 3 is a block functional diagram of the pacemaker illustrated in FIG. 1, as connected to a human heart 10. The circuitry illustrated is all located within the conductive housing or can 8 of the pacemaker, as illustrated in FIG. 1, and the bipolar leads 14 and 16 are illustrated schematically as coupled directly to the circuit. However, of course, in the actual device they would be coupled by means of removable electrical connectors inserted in the connector block 12, as illustrated in FIG. 1.

The pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14, as well as an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16 as well. The ventricular sense amplifier provides for separate detection and identification of QRSowave signals, in a known manner; it may also provide for detection and identification of T-wave signals. The atrial sense amplifier provides for respective identification of P-waves and FFRS signals. The output circuit 340 and sense amplifier circuit 360 may contain pulse generators and sense amplifiers corresponding to any of those presently employed in commercially marketed cardiac pacemakers. Control of timing and other functions within the pacemaker circuit is provided by digital controller/timer circuit 300, which includes a set of timers and associated logic. Digital controller/timer circuit 330 defines the basic pacing interval of the device, which may take the form of an A—A escape interval initiated on atrial sensing or pacing and triggering atrial pacing at the expiration thereof, or may take the form of a V—V escape interval, initiated on ventricular sensing or pacing and triggering ventricular pulse pacing at the expiration thereof. Digital controller/timer circuit 330 similarly defines the A-V escape interval, $AV_{esc}$, discussed in detail below. The specific values of the intervals defined are controlled by the microcomputer circuit 302 by means of data and control bus 306. Sensed atrial depolarizations and FFRSs are communicated to the digital controller/timer circuit 330 on A event line 352; and ventricular depolarizations (QRS-waves) are communicated to the digital controller/timer circuit 330 on V event line 354. In order to trigger generation of a ventricular pacing pulse, digital controller/timer circuit 330 generates a trigger signal on V trig line 342. Similarly, in order to trigger an atrial pacing pulse, digital controller/timer circuit 330 generates a trigger pulse on a trig line 344.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 330 will also define an atrial refractory period during which atrial sensing is disabled, this refractory period extending from the beginning of the A-V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/timer circuit 330 also controls sensitivity settings and timing windows of the sense amplifiers 360 by means of sensitivity control 350. The timing windows are used, e.g., for separating out R-wave or FFRS-wave portions for use in the control algorithm of FIG. 6.

In the embodiment illustrated in FIG. 2, the pacemaker is provided with a piezo electric sensor 316 which is intended to monitor patient activity, in order to allow provision of rate responsive pacing, such that the defined pacing rate (A—A escape interval or V—V escape interval) increases with increased demand for oxygenated blood. Sensor 316 generates electrical signals in response to sensed physical activity which are processed by activity circuit 322 and provided to digital controller/timer circuit 330. Activity circuit 332 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Transmission to and from the external programmer 4 illustrated in FIG. 2 is accomplished by means of antenna 334 and associated RF transmitter and receiver 322, which serves both to demodulate received downlink telemetry and to transmit uplink telemetry. Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers.

Microcomputer circuit 302 controls the operational functions of digital controller/timer 330, specifying which timing intervals are employed, and controlling the duration of the various timing intervals, via data and control bus 306. Microcomputer circuit 302 contains a microprocessor 304 and associated system clock 308 and on processor RAM circuits 310 and 312, respectively. In addition, microcomputer circuit 302 includes a separate RAM/ROM chip 3 14. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every cycle or every two seconds, may be provided in order to allow the microprocessor to analyze the sensor data and update the basic rate interval (A—A or V—V) of the device. In addition, in a preferred embodiment of the invention, the microprocessor 304 may also serve to define variable A-V escape intervals and atrial and ventricular refractory periods which may also decrease in duration along with decreases in duration of the basic rate interval. Specifically, the microprocessor is used to carry out the routines illustrated in FIGS. 4 and 6.

The illustrated circuitry of FIG. 3 is merely exemplary, and corresponds to the general functional organization of most microprocessor controlled cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microprocessor circuit 302. However, the present invention many also be usefully practiced by means of a full custom integrated circuit, or any combination of hardware and software.

Figure 4:
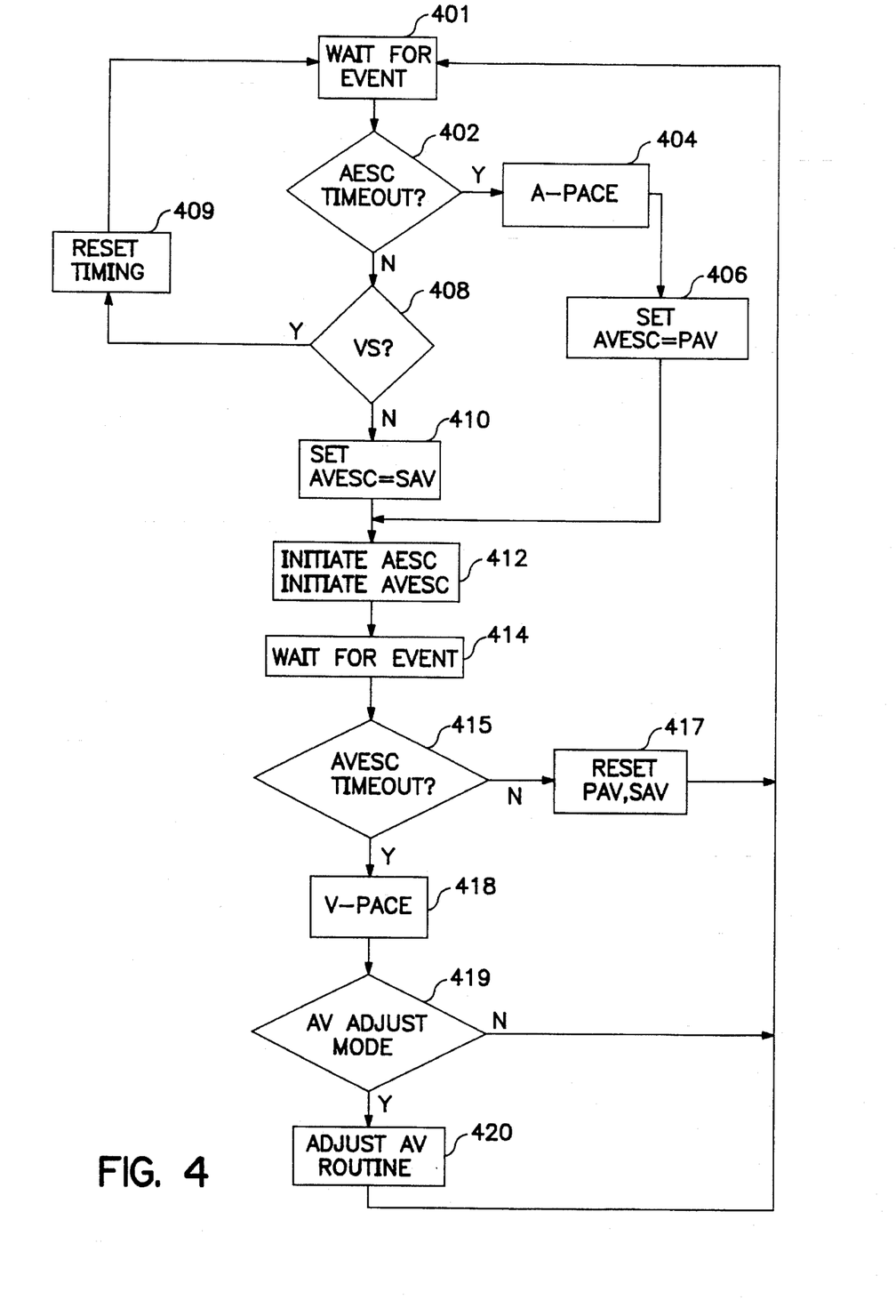
FIG. 4 is a generalized flow diagram illustrating steps taken in synchronous pacing in accordance with this invention, including adjusting AV escape interval for optimizing HOCM therapy.

Referring now to FIG. 4, there is shown a generalized flow diagram of steps taken by a pacemaker system in accordance with this invention in performing synchronous pacing, with adjustment of $AV_{esc}$ for optimal HOCM therapy. The steps of this flow diagram are suitably carried out by microcomputer circuit 302. This is a simplified flow diagram setting forth only steps pertinent to controlling $AV_{esc}$, and does not include many other steps and responses that occur during each cycle of a typical dual chamber pacemaker. The illustrated logic of FIG. 4 recognizes that the intrinsic AV conduction time following an atrial pace pulse is greater than following a sensed atrial depolarization, by an amount described as "atrial sense offset", or ASO in referenced U.S. application Ser. No. 08/214,933, now U.S. Pat. No. 5,507,782. The $AV_{esc}$ following an atrial pace is defined as PAV; $AV_{esc}$ following an atrial sense is defined as SAV; and PAV=SAV+ASO.

At block 401, the routine of FIG. 4 is waiting for what is expected to be an atrial event. When an event occurs, the routine goes to block 402 and determines whether there has been timeout of the atrial escape interval, $A_{esc}$. If yes, this indicates that an atrial pace (AP) should be delivered, and this is done at block 404. Following this, the routine sets $AV_{esc}$ to PAV, and initiates timeout of $AV_{esc}$. Returning to 402, if there has been no timeout of $A_{esc}$, the pacemaker proceeds to 408, and determines whether there has been an early ventricular sense (VS). If yes, the routine branches to block 409 and resets the timing appropriately, whereafter it returns to block 401. However, as would normally be the case, if at 408 the event is not a VS, meaning that it has been an atrial sense (AS), the routine proceeds to block 410 and sets $AV_{esc}$ to the current value of SAV Following this, the routine goes to 412 and initiates timeout of the atrial escape interval ($A_{esc}$), and timeout of the AV escape interval, $AV_{esc}$ (either SAV or PAV). Then, at 414, the pacer waits for the next event, normally a ventricular event.

At 415, the pacemaker responds to an event by first determining whether the event was a timeout of $AV_{esc}$. If no, meaning that there was a ventricular sense, the pacemaker proceeds to block 417 and resets PAV and SAV to a shorter value which ensures capture by the next ventricular pace pulse. For example, each of these values can be decremented by 20 or 50 ms, to ensure that succeeding timeouts of $AV_{ees}$ occur early enough for complete capture. It is to be noted, however, that the algorithms discussed below are designed to avoid an occurrence of VS, such that the pacemaker should rarely take this path.

If at 415 there has been a timeout of $V_{esc}$, then the pacemaker proceeds to block 418 and delivers a V pace. Then, at block 419, the pacemaker determines whether it is programmed to go into the AV adjust routine. If no, the routine is done and it exists back to 401. If yes, the pacemaker goes to the adjust AV routine at block 420. Here, the pacemaker analyzes collected data, e.g., VP-FFRS time; FFRS duration; or FFRS or QRS amplitude. With this data in hand, the pacemaker system can adjust the values of PAV and SAV, in accordance with a predetermined algorithm for changing $AV_{esc}$ so as to optimize resultant pre-excitation. Following this, the routine returns to block 401 and waits for the next atrial event.

Note that the pacemaker can be programmed for automatically monitoring AV data and adjusting $AV_{esc}$ each pacemaker cycle, or these steps can be taken on some other periodic or user-programmed basis, within the scope of the invention. For an implanted pacemaker which is set to automatically adjust AV, the pacemaker goes directly to 420. Similarly, for a pacemaker system in accordance with this invention which adapted to be programmed specifically by a physician, the routine exits unless the programming sequence has been activated.

Figure 5:
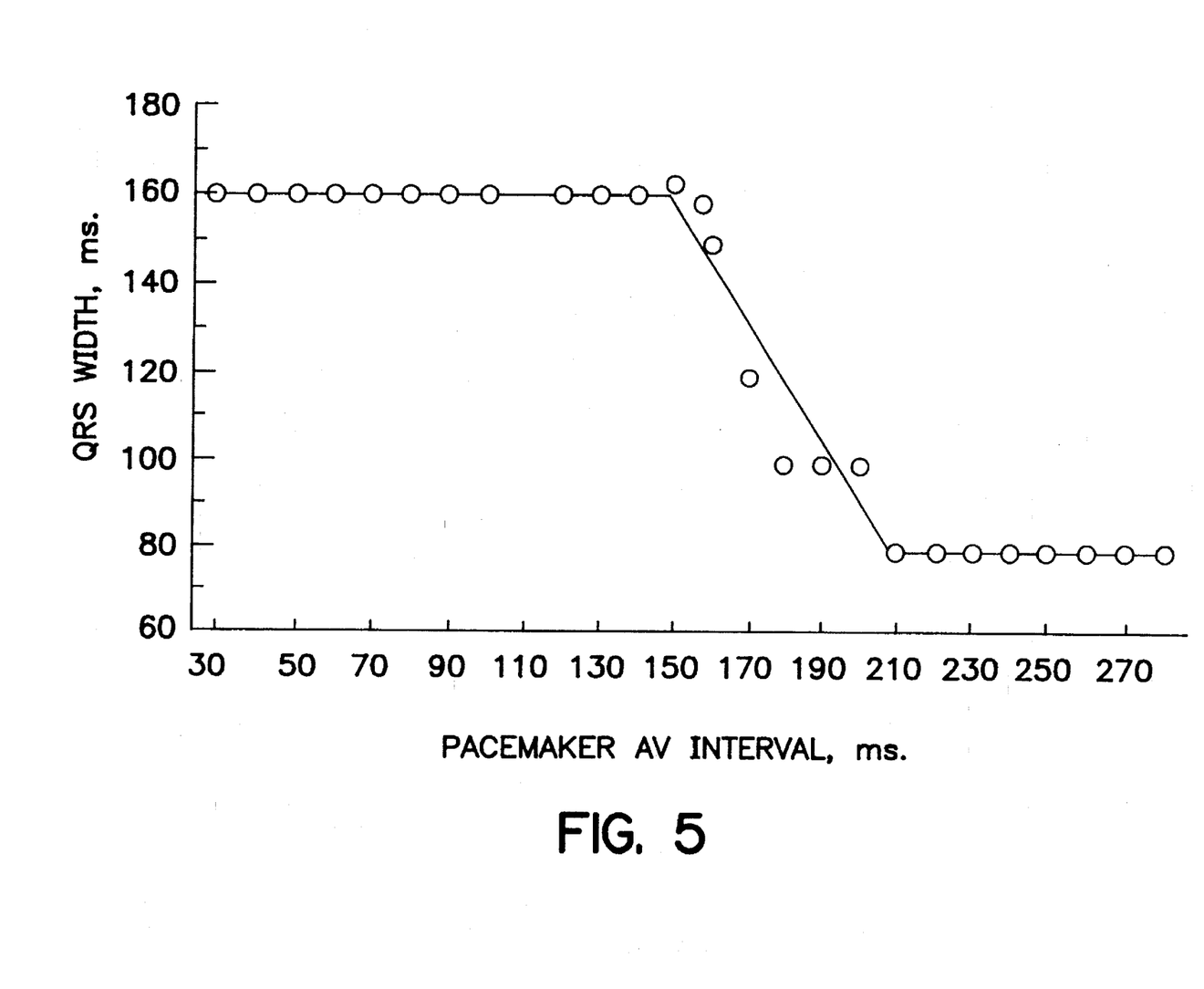
FIG. 5 is a representative data plot of QRS or FFRS duration as a function of pacemaker AV escape interval.

Referring now to FIG. 5, there is shown a plot of data representative of QRS or FFRS duration (ms) as a function of pacemaker AV escape interval (ms). As is seen in FIG. 5, the QRS duration is relatively low at higher AV intervals which are greater than the patient's intrinsic PR conduction time, i.e., where a VS occurs before timeout of $AV_{esc}$. However, as $AV_{esc}$ is shortened, it comes into a fusion area where QRS increases to a maximum value. At shorter intervals, where a VP results in full capture, QRS duration is substantially constant, at or near the maximum value. The knee portion between full capture and failure to capture is termed the fusion area, or range, and the ability to detect QRS duration changes in this area, provides the basis for one embodiment of this invention. As used herein, the term "fusion" embraces the entire knee range, including the lower portion of the range, referred to as "onset of fusion."

Figure 6:
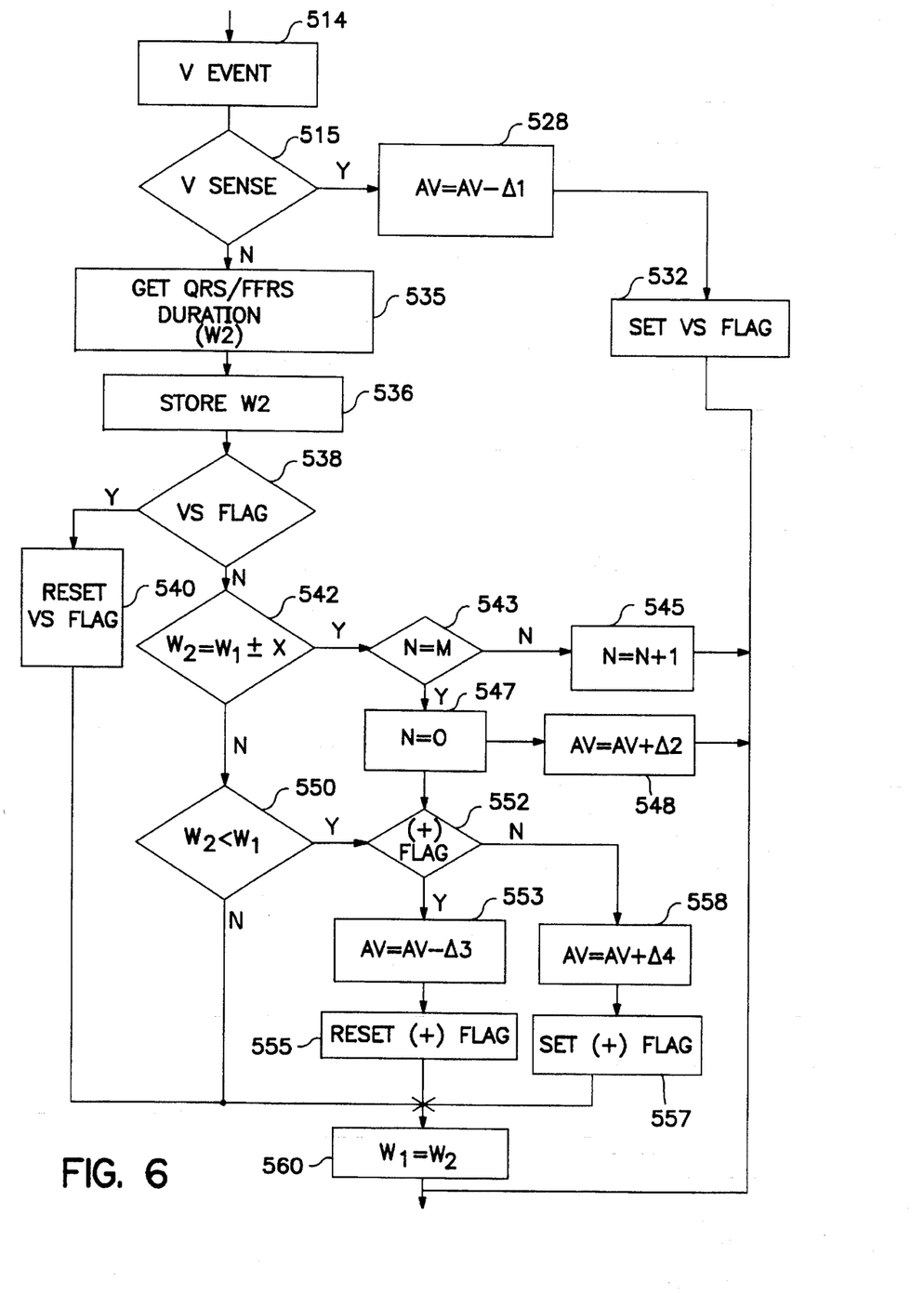
FIG. 6 is a detailed flow diagram showing the steps carried out by the pacemaker system and method of this invention in automatically adjusting AV escape interval in a closed loop fashion for optimized HOCM or CHF therapy.

Referring now to FIG. 6, there is shown a flow diagram setting forth the primary steps which can be taken each cycle by the pacemaker system in accordance with this invention, for adjusting the AV interval so as to maintain that interval just short of fusion. Although the flow diagram shows steps for automatic adjustment on a cyclical basis, it is to be understood that the program may be initiated by an external programmer or may be carried out only periodically by an implantable or external pacemaker. Depending upon the configuration employed, QRS or FFRS data is obtained either from 30 ECG leads, or implanted leads 14 or 16.

After a ventricular event, illustrated at 514, the pacemaker determines at 515 whether there has been a V sense. If yes, this indicates that the AV delay is too long, and the routine decrements AV by Δ1 at block 528. The value of Δ1 may be in the range of 20–50 ms. After this, at 532 the pacemaker sets a VS flag, indicating that there was a V-sense in the last cycle, and then exits. If at 515 it is determined there has been no V-sense, such that the V event was a V pace, the algorithm proceeds to block 535. At this point, the pacemaker obtains the duration of the QRS or FFRS evoked by the pace pulse, designated W2. As set forth above, the duration or width of the QRS signal may be obtained from the V sense channel by suitable processing of the sensed QRS signal. Alternately, it can be obtained from the A sense channel, by a processing of the FFRS signal. For determining width of the QRS or FFRS, the signal is suitably processed with standard circuitry in circuit 330 to determine when it first rises to a predetermined level, and when it falls back below such level. Note that the actual signal may be a deviation from some existing baseline, not necessarily positive. In discussing the rise and fall of the signal, it is understood that his refers to deviations from a noise-adjustment signal floor. These circuits may be supplemented or replaced by known digital processing techniques carried out with the aid of microprocessor system 302. Following the duration measurement, the value of the just determined W2 is stored, at 536. The pacemaker then determines at 538 whether the VS flag is set. If yes, meaning that there was a VS in the prior cycle, the routine branches to 540 and resets the VS flag, and then jumps directly to 560 and sets $W_1$ equal to the value of W for the prior cycle (i.e., $W_1=W_2$). Note that there is no increment or decrement of AV at this point, since no value of W2 had been obtained during the prior cycle.

Returning to block 538, if the VS flag is not set, the routine proceeds to block 542, and compares $W_2$, the duration just determined, with the prior duration value, $W_1$. More specifically, the determination is made as to whether $W_2$ is equal to $W_1$ plus or minus x, where x is a variable to account for jitter and other measurement variations. If the signals are substantially equal, the routine branches to block 543 and determines whether a variable N equals fixed value M. If no, N is incremented at block 544. However, if N=M, this means that the duration value has been substantially constant for M cycles. The routine then branches to block 547 and sets N=0, and then proceeds to block 548 and increments AV by $\Delta 2$, where $\Delta 2$ is suitably 2–10 ms. This step corresponds to the situation where the pacemaker AV escape interval is in the range of values less than the fusion range, and with a substantially constant duration. Under these circumstances, the invention acts to increment the AV escape interval to move it toward the knee of the curve.

Returning to block 542, if the duration is found not to be substantially equal to the duration of the prior cycle, the routine goes to 550 and determines whether the most recent duration ($W_2$) is less than the prior duration ($W_1$). If yes, this means that the value of $AV_{esc}$ has moved away from the maximal point indicated in FIG. 5. The routine goes to 552 and determines whether the (+) flag has been set, which indicates that the last adjustment of AV interval was an increment. If yes, this means that the pacemaker is operating at an AV escape interval to the right of the peak as indicated in FIG. 5. The routine branches to 553, and decrements AV escape interval by $\Delta 3$. $\Delta 3$ is suitably set to a value relative to the fusion range so as to bring AV well back toward the maximal value, and even suitably to a value shorter than the fusion knee, e.g., 10–15 ms. After this, the (+) flag is reset at 555, and $W_1$ is set equal to $W_2$ at 560. Returning to 552, if the (+) flag was not set, meaning that the last adjustment of $AV_{esc}$ was to decrement it, the routine branches to 557 and increments AV by $\Delta 4$. This corresponds to a pacemaker operation on the left side of the curve with respect to the maximal point. $\Delta 4$ is suitably a value less than $\Delta 3$, e.g. 2–5 ms, and is chosen to maintain operation near the peak or just to the short side of the peak value as seen in FIG. 5. Following this, since AV has just been incremented, the (+) flag is set at 558, and $W_1$ is set equal to $W_2$ at 560.

Looking again at 550, if $W_2$ is not determined to be less than $W_1$, i.e., $W_2$ is greater than $W_1$, this means that pacemaker operation has proceeded toward the maximum point on the curve, from either direction. In this situation, no change in $AV_{ees}$ is desired, and accordingly the routine exits. Since $\Delta 3$ is greater than $\Delta 4$, the closed loop control continually drives $AV_{esc}$ to a value just less than that corresponding to maximum duration, or just at the edge of "onset of fusion."

There has thus been disclosed a pacemaker system and method for automatic adjustment of AV escape interval for optimizing pre-excitation by the delivered ventricular pace pulses. In a preferred embodiment of this invention, the pacemaker system continuously detects, on a cyclical basis, the duration of the evoked QRS signal, obtaining such signal either directly from a ventricular sense channel, or from FFRS signals derived from the atrial sense channel. The control algorithm continuously compares the duration data for successive cycles, and adjusts the AV escape interval as a function of the compared durations as well as a function of the direction of the last adjustment of AV escape interval. Although the preferred embodiment has illustrated automatic adjustment on a cyclical basis, it is to be understood that it is with in the scope of the invention to adjust on a non-cyclical basis, e.g., by collecting data over a predetermined number of cycles, and adjusting based on comparisons of collected durations. Thus, for example, duration can be obtained as an average of the individual durations over n cycles, and the comparisons made every such n cycles.

What is claimed is:

1. A dual chamber pacemaker system, having atrial sense means for sensing signals from a patient's atrium, ventricular sense means for sensing ventricular signals from a patient, ventricular pace means for generating and delivering ventricular pace pulses to said patient's right ventricle, $AV_{esc}$ means for setting and timing out an AV escape interval from the occurrence of the sensed atrial depolarization, and sync control means for controlling delivery of a ventricular pace pulse at the time out of a said AV escape interval in the absence of a sensed ventricular signal, comprising wave means for obtaining and storing representations of QRS waves that have been evoked by delivered ventricular pace pulses, controllable adjust means for adjusting said $AV_{esc}$ means to vary said AV escape interval in a controlled direction, and storage means for storing a representation of said direction, change means for detecting a change of successive such QRS representations, and control means for controlling said adjust means as a function of said detected change and said stored direction.

2. The pacemaker system as described in claim 1, wherein said obtaining means comprises means for cyclically obtaining a representation of the duration of the QRS wave, and said change means has means for comparing each QRS representation with the QRS representation of the prior cycle.

3. The pacemaker system as described in claim 1, wherein said change means comprises means for determining when said representation changes from the prior representation by more than a predetermined amount.

4. The pacemaker system as described in claim 1, wherein control means has means for controlling said adjust means to decrement AV escape interval by a first factor when said stored direction is to shorten AV escape interval, and by a second factor when said stored direction is to increment AV escape interval.

5. The pacemaker system as described in claim 4, wherein said first factor is greater than said second factor.

6. The pacemaker system as described in claim 1, wherein said representation is QRS duration, the variation of QRS duration with AV escape interval having a range of variation defining a fusion range, and wherein said control means controls said adjust means to adjust said AV escape interval toward maintaining AV escape interval at a value within the lower portion of said fusion range.

7. The pacemaker system as described in claim 1, further comprising means for detecting when there has been no substantial change of said representation from one cycle to the next, and wherein said control means generally maintains said AV escape interval constant when there has been no substantial change.

8. The pacemaker system as described in claim 7, further comprising determining means for determining when there has been no substantial change in said QRS representation over a predetermined plurality of pacemaker cycles, and second change means for incrementing said AV escape interval in response to a said determination.

9. The pacemaker system as described in claim 1, comprising FFRS means for detecting FFRS signals, and wherein said wave means comprises means for obtaining said QRS representations from said detected FFRS signals.

10. A method of dual chamber cardiac 5pacing for heart pacing therapy, comprising sensing the occurrence of natural atrial beats, initiating timeout of an AV escape interval following a sensed atrial beat and delivering a ventricular pace pulse at the timeout of a said AV escape interval in the absence of a sensed ventricular natural beat, and controlling said AV escape interval in a direction to maximize the number of delivered ventricular pace pulses that evoke complete capture of the heart and to maximize the AV escape interval, said method including:

obtaining a measure of the duration of each evoked QRS, and storing said measure, comparing the measure of each QRS duration with the stored value of the prior QRS duration and determining when said compared values differ by more than a predetermined amount, and adjusting said AV escape interval in a determined lengthening or shortening direction as a function of said comparison.

11. The method as described in claim 10, comprising storing said determined direction, and wherein said adjusting step further comprises determining said direction as a function of the stored direction from the prior pacemaker cycle.

12. The method as described in claim 11, wherein said adjusting step comprises decrementing AV escape interval by a first predetermined amount when QRS duration has decreased following a prior increase in AV escape interval.

13. The method as described in claim 12, wherein said adjusting step comprises incrementing AV escape interval by a second predetermined amount when QRS duration has decreased following a prior decrement of AV escape interval.

14. The method as described in claim 13, wherein said first amount is greater than said second amount.

15. A method of dual chamber pacing for cardiomyopathy therapy, comprising:

cyclically collecting QRS characteristic data;

determining and storing the differences of said data for respective pairs of successive cycles;

adjusting AV escape interval as a function of said differences and storing the direction of each adjustment, and said adjusting step including determining the direction of the adjustment as a function of the direction of the last such adjustment.

16. A dual chamber pacemaker having atrial sense means for sensing signals in a patient's atrium, ventricular sense means for sensing signals in said patient's ventricle, ventricular pace means for generating and delivering ventricular pace pulses to the patient's ventricle, and AV control means for controlling said pace means to generate and deliver a ventricular pace pulse at a controlled AV escape interval following a sensed atrial signal, comprising:

means for continually monitoring a measure of the duration of the QRS signal sensed by either said atrial sense means or said ventricular sense means, first determining means for continually determining whenever said duration measure is shorter than a prior duration measure, and adjustment means for decrementing said AV escape interval by a first value in response to a determination by said determining means; and second determining means for determining when said duration measure has been substantially constant for a predetermined time, and wherein said adjustment means further comprises increment means for incrementing said AV escape interval by a second value in response a said substantially constant determination.

17. The pacemaker as described in claim 16, wherein said first interval is greater than said second interval.

18. The pacemaker as described in claim 16, wherein said first determining means is operative each pacemaker cycle.

19. The pacemaker as described in claim 16, wherein said second determining means has periodic means for making said determination periodically.

20. The pacemaker as described in claim 19, wherein said periodic means makes said determination every n cycles.

* * * * *